United States Patent [19]

Wright, Jr. et al.

[11] Patent Number: 4,680,293
[45] Date of Patent: Jul. 14, 1987

[54] 3-IMIDAZOLYLALKYL-, TRIAZOLYLALKYL-, PYRIDINYLALKYL-1,2,3-BENZOTRIAZIN-4(3H)-ONES AND DERIVATIVES THEREOF

[75] Inventors: William B. Wright, Jr.; Andrew S. Tomcufcik, both of Bergen, N.J.; Joseph W. Marsico, Jr., Rockland, N.Y.

[73] Assignee: American Cyanamid Company, Stamford, Conn.

[21] Appl. No.: 835,501

[22] Filed: Mar. 3, 1986

[51] Int. Cl.[4] .................... A61K 31/53; C07D 253/08
[52] U.S. Cl. ..................................... 514/243; 544/183
[58] Field of Search ..................... 544/183; 514/243

[56] References Cited

U.S. PATENT DOCUMENTS 3,706,739 12/1972 Beyerle et al. ............... 544/183 X
3,751,413  8/1973 Stachel et al. ............... 544/183
3,808,318  4/1974 Kathawala .................. 514/243 X

FOREIGN PATENT DOCUMENTS 1957319 11/1969 Fed. Rep. of Germany .

Primary Examiner—Joseph Paul Brust
Attorney, Agent, or Firm—Susan H. Rauch

[57] ABSTRACT

Novel 3-heteroarylalkyl-1,2,3-benzotriazin-4(3H)-ones, having the structural formula:

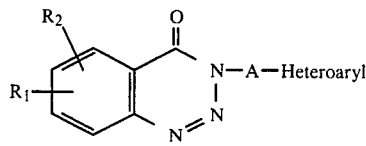

wherein A is a divalent moiety of the formula:

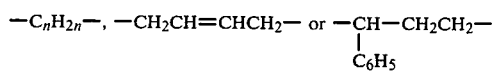

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

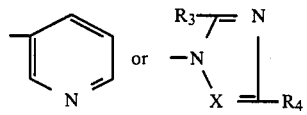

wherein $R_3$ and $R_4$ may be hydrogen, alkyl having from one to four carbon atoms or phenyl and X is CH or N; together with the pharmaceutically acceptable salts thereof; processes for their preparation and their use in treating prostaglandin-related vascular disorders including ischemic heart disease, transient ischemic attack, thrombosis, migraine and hypertension.

20 Claims, No Drawings

3-IMIDAZOLYLALKYL-, TRIAZOLYLALKYL-, PYRIDINYLALKYL-1,2,3-BENZOTRIAZIN-4(3H)-ONES AND DERIVATIVES THEREOF

BRIEF SUMMARY OF THE INVENTION

This invention relates to new organic compounds and, more particularly, is concerned with novel 3-(ω-heteroarylalkyl)-1,2,3-benzotriazin-4(3H)-ones which may be represented by the following structural formula:

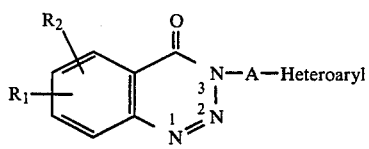

wherein A is a divalent moiety of the formula:

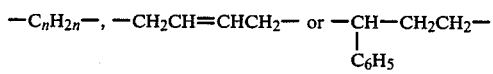

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

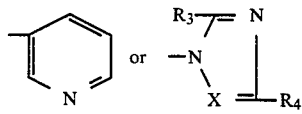

wherein $R_3$ and $R_4$ may be hydrogen, alkyl having from one to four carbon atoms or phenyl; and X is CH or N.

A preferred embodiment of the present invention may be represented by the following structural formula:

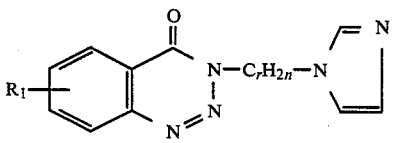

wherein $R_1$ and n are as hereinbefore defined. Most preferably, $R_1$ is chlorine and n is 4.

The organic bases of this invention form non-toxic acid-addition salts, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the like.

For purposes of this invention the free bases are equivalent to their non-toxic acid-addition salts. The acid-addition salts of the organic bases of the present invention are, in general, relatively soluble in water, methanol and ethanol but relatively insoluble in nonpolar organic solvents such as diethyl ether, benzene, toluene, and the like.

DETAILED DESCRIPTION OF THE INVENTION

The novel compounds of the present invention may be readily prepared as set forth in the following reaction scheme wherein $R_1$, $R_2$, n, A and Heteroaryl are as hereinabove defined.

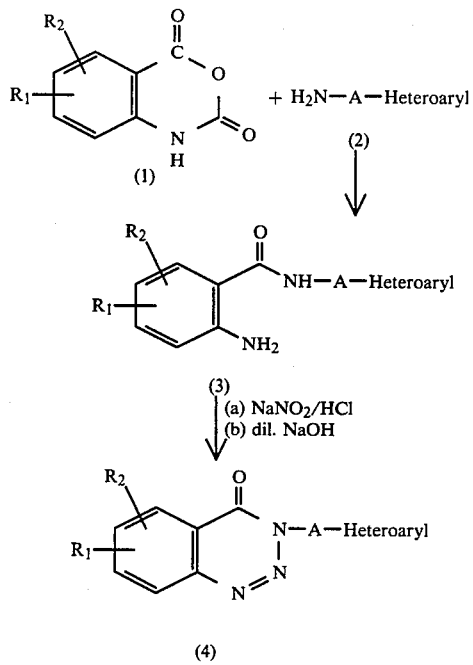

In accordance with this method, an appropriately substituted isatoic anhydride (1) is reacted with a heterocyclic alkanamine (2) in an inert solvent such as toluene, ethanol or dimethyl sulfoxide at ambient or reflux temperature to form the intermediate amide (3). Treatment of (3) with sodium nitrite in dilute hydrochloric acid for 1-3 hours at a preferred temperature of 0°-30° C. then neutralization with dilute sodium hydroxide results in the desired compounds (4).

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin, such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects,* H. Barnett, P. Paoletti, E. Flamm and G. Brambilla, eds., Elsevier/North-Holland Biomedical Press, pp 137-150 (1981)]. Prostacyclin ($PGI_2$) is a potent vasodilator and platelet aggregation inhibitor, whereas thromboxane ($TXA_2$) is a powerful vasoconstrictor and inducer of platelet aggregation. $TXA_2$ synthesis is catalyzed by thromboxane synthetase enzyme located in, for example, blood platelets. When $TXA_2$ production is increased relative to $PGI_2$, platelet aggregation, thrombosis and vasospasm may occur [*Lancet* (i), 1216 (1977); *Lancet,* 479 (1977); *Science,* 1135 (1976); *Amer. J. Cardiology,* 41, 787 (1978)]. $TXA_2$ synthetase inhibitors have been shown to have anti-thrombotic action superior to that of aspirin [*J. Clin. Invest.*, 65, 400 (1980); *Br. J. Pharmac.*, 76, 3 (1982)].

The role of prostaglandins, including $TXA_2$ and $PGI_2$, in ischemic heart patients has been reviewed [*Cardiovascular Pharmacology of the Prostaglandins*, A. G. Herman, P. M. Vanhoute, H. Denolin and A. Goosens, eds., Raven Press, New York, pp 361-374 (1982)]. Injection of $TXA_2$ into coronary arteries of guinea pigs and rabbits causes myocardial ischemia and subendocardial necrosis [*Drugs of the Future*, 7, 331 (1982); *Proc. Jap. Acad.*, 53(B), 38 (1977); *Eur. J. Pharmacol.*, 53, 49 (1978)]. Recent research has demonstrated the beneficial effects of $PGI_2$ and selective inhibition of thromboxane synthetase on ischemic myocardium in canines [*J. Cardiovascular Pharmacology*, 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

From Okamoto-Aoki spontaneously hypertensive rats (SHR) (Taconic Farms, Germantown, NY) between 19 and 24 weeks in age, under urethane anesthesia, 10 μl of arterial blood was collected in one ml of 3.2% sodium citrate in a polystyrene tube. The blood was diluted with 3 ml cold saline and centrifuged at room temperature for 15 minutes at $460 \times g$. The platelet rich plasma (PRP) was separated. The platelets were isolated by centrifuging the PRP for 10 minutes at $1060 \times g$ and were washed in 4 ml cold oxygenated Krebs phosphate buffer, pH 7.4. The chilled platelets recovered from centrifuging at $800 \times g$ for 10 minutes were resuspended in oxygenated Krebs phosphate buffer and diluted to contain $4.5-6.0 \times 10^4$ platelets/μl.

The inhibition of thromboxane (TX) formation was studied by determining the concentration of thromboxane $B_2$ ($TXB_2$), the stable hydrolysis product of $TXA_2$. Assay samples, prepared on ice, contained 200 μl platelet suspension, 50 μl saline, and 50 μl vehicle or drug under study at a concentration of $10^{-4}$M (with OKY-1581, UK-37248-01, 1-benzylimidazole, and/or indomethacin used as standards). The samples were incubated for 10 minutes at 37° C. in a metabolic shaker. The reaction was terminated by immersing the tubes in an ice bath and adding 50μ of 0.5M citric acid. The samples were centrifuged for 10 minutes in a refrigerated centrifuge and the supernatants thus obtained were decanted and stored at −20° C. The $TXB_2$ content for each sample was determined by a direct radioimmunoassay (RIA) utilizing a $TXB_2$ specific RIA kit purchased from New England Nuclear, Boston, MA and results expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Compound | % Inhibition |
| --- | --- |
| 3-[3-(1H—Imidazol-1-yl)propyl]-1,2,3-benzotriazin-4(3H)—one | 97 |
| 3-[4-(1H—Imidazol-1-yl)butyl]-1,2,3-benzotriazin-4(3H)—one | 68 |
| 3-[5-(1H—Imidazol-1-yl)pentyl]-1,2,3-benzotriazin-4(3H)—one, monohydrochloride | 67 |
| 3-[6-(1H—Imidazol-1-yl)hexyl]-1,2,3-benzotriazin-4(3H)—one, monohydrochloride | 96 |
| 3-[3-(1H—Imidazol-1-yl)-2-methylpropyl]-1,2,3-benzotriazin-4(3H)—one, monohydrochloride | 92 |

TABLE I-continued

| Compound | % Inhibition |
| --- | --- |
| 6-Chloro-3-[3-(1H—imidazol-1-yl)propyl]-1,2,3-benzotriazin-4(3H)—one | 74 |
| 6-Chloro-3-[4-(1H—imidazol-1-yl)butyl]-1,2,3-benzotriazin-4(3H)—one, monohydrochloride | 97 |
| 6-Chloro-3-[5-(1H—imidazol-1-yl)pentyl]-1,2,3-benzotriazin-4(3H)—one | 82 |
| 6-Chloro-3-[6-(H—imidazol-1-yl)hexyl]-1,2,3-benzotriazin-4(3H)—one | 73 |
| 6-Chloro-3-[8-(1H—imidazol-1-yl)octyl]-1,2,3-benzotriazin-4(3H)—one, monohydrochloride | 90 |
| 6-Chloro-3-[10-(1H—imidazol-1-yl)decyl]-1,2,3-benzotriazin-4(3H)—one, fumarate | 80 |
| 6-Chloro-3-[3-(1H—imidazol-1-yl)-2-methylpropyl]-1,2,3-benzotriazin-4(3H)—one, monohydrochloride | 93 |
| 6-Chloro-3-[3-(4-methyl-1H—imidazol-1-yl)propyl]-1,2,3-benzotriazin-4(3H)—one | 85 |
| 7-Chloro-3-[4-(1H—imidazol-1-yl)butyl]-1,2,3-benzotriazin-4(3H)—one | 90 |
| 6,8-Dichloro-3-[4-(1H—imidazol-1-yl)butyl]-1,2,3-benzotriazin-4(3H)—one, monohydrochloride | 93 |
| 6-Bromo-3-[4-(1H—imidazol-1-yl)butyl]-1,2,3-benzotriazin-4(3H)—one, monohydrochloride | 96 |
| 6-Bromo-3-[3-(1H—imidazol-1-yl)-2-methylpropyl]-1,2,3-benzotriazin-4(3H)—one | 99 |
| 3-[4-(1H—imidazol-1-yl)butyl]-6-methyl-1,2,3-benzotriazin-4(3H)—one | 95 |
| 3-[3-(1H—Imidazol-1-yl)-2-methylpropyl]-6-methyl-1,2,3-benzotriazin-4(3H)—one, monohydrochloride | 95 |
| 3-[4-(1H—Imidazol-1-yl)butyl]-7,8-dimethyl-1,2,3-benzotriazin-4(3H)—one, monohydrochloride | 93 |
| 3-[4-(1H—Imidazol-1-yl)butyl]-8-trifluoromethyl-1,2,3-benzotriazin-4(3H)—one | 86 |
| 3-[5-(1H—Imidazol-1-yl)pentyl]-8-trifluoromethyl-1,2,3-benzotriazin-4(3H)—one | 87 |
| 3-[3-(1H—Imidazol-1-yl)-2-methylpropyl]-6-nitro-1,2,3-benzotriazin-4(3H)—one | 95 |
| 3-[4-(3-Pyridinyl)butyl]-1,2,3-benzotriazin-4(3H)—one | 75 |
| 6-Chloro-3-[4-(3-pyridinyl)butyl]-1,2,3-benzotriazin-4(3H)—one | 85 |
| 6-Chloro-3-[3-(1H—imidazol-1-yl)-2-methylpropyl]-1,2,3-benzotriazin-4(3H)—one | 97 |
| 6-Chloro-3-[4-(1H—imidazol-1-yl)butyl]-1,2,3-benzotriazin-4(3H)—one | 79 |

The novel compounds of the present invention are also active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, NY, having an average mean arterial blood pressure of $160 \pm 1.5$ mm of mercury are used in the test. One to 3 rats were used per test compound. The rats were dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure (MABP) was measured by the method of Chan and Poorvin vide supra. The procedure was repeated in a second and third rat when necessary as specified in the referenced method.

The results of this test on representative compounds of the present invention appear in Table II below.

TABLE II

| Product | MABP/mmHg (no. of rats) |
|---|---|
| 3-[3-(1H—Imidazol-1-yl)propyl]-1,2,3-benzotriazin-4(3H)—one | 111(2) |
| 3-[4-(1H—Imidazol-1-yl)butyl]-1,2,3-benzotriazin-4(3H)—one | 114(2) |
| 3-[5-(1H—Imidazol-1-yl)pentyl]-1,2,3-benzotriazin-4(3H)—one, monohydrochloride | 113(2) |
| 3-[6-(1H—Imidazol-1-yl)hexyl]-1,2,3-benzotriazin-4(3H)—one, monohydrochloride | 87(2) |
| 6-Chloro-3-[3-(1H—imidazol-1-yl)propyl]-1,2,3-benzotriazin-4(3H)—one | 127(3) |
| 6-Chloro-3-[4-(1H—imidazol-1-yl)butyl]-1,2,3-benzotriazin-4(3H)—one | 105(2) |
| 6-Chloro-3-[5-(1H—imidazol-1-yl)pentyl]-1,2,3-benzotriazin-4(3H)—one | 117(2) |
| 6-Chloro-3-[6-(1H—imidazol-1-yl)hexyl]-1,2,3-benzotriazin-4(3H)—one | 109(2) |
| 6-Bromo-3-[4-(1H—imidazol-1-yl)butyl]-1,2,3-benzotriazin-4(3H)—one, monohydrochloride | 115(2) |
| 3-[4-(1H—Imidazol-1-yl)butyl]-6-methyl-1,2,3-benzotriazin-4(3H)—one | 106(2) |
| 3-[4-(1H—Imidazol-1-yl)butyl]-7,8-dimethyl-1,2,3-benzotriazin-4(3H)—one, monohydrochloride | 121(2) |
| 3-[3-(1H—Imidazol-1-yl)-2-methylpropyl]-6-nitro-1,2,3-benzotriazin-4(3H)—one | 114(2) |
| 6-Chloro-3-[8-(1H—imidazo-1-yl)octyl]-1,2,3-benzotriazin-4(3H)—one, monohydrochloride | 116(2) |

The novel compounds of the present invention have been found to be highly useful for inhibiting thromboxane synthetase and also for lowering elevated blood pressure in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic adminstration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate. A sweetening agent such as sucrose, lactose or saccharin or a flavoring agent such as peppermint, oil of wintergreen or cherry flavoring may be added. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor or the equivalents thereof. Of course, any material used in preparing any dosage unit form should be pharmaceutically pure and substantially nontoxic in the amounts employed.

The following specific examples illustrate the preparation of the compounds of the present invention.

EXAMPLE 1

2-Amino-N-[4-(1H-imidazol-1-yl)butyl]benzamide

A mixture of 1.63 g of isatoic anhydride, 1.39 g of 1H-imidazole-1-butanamine and 25 ml of ethanol was stirred at room temperature for 22 hours. The reaction mixture was concentrated and the residue was dissolved in ethyl acetate and cooled. The desired product was isolated by filtration, mp 91°–93° C.

Following the procedure of this example and using the appropriate isatoic anhydride derivative, the products of Examples 2–7 were obtained as set forth in Table III.

TABLE III

| Ex. | Isatoic Anhydride | Product | MP °C. |
| --- | --- | --- | --- |
| 2 | 5-Bromo | 2-Amino-5-bromo-N—[4-(1H—imidazol-1-yl)butyl]benzamide | 108–110 |
| 3 | 5-Chloro | 2-Amino-5-chloro-N—[4-(1H—imidazol-1-yl)butyl]benzamide | 91–94 |
| 4 | 5-Methyl | 2-Amino-N—[4-(1H—imidazol-1-yl)butyl]-5-methylbenzamide | 79–81 |
| 5 | 3,4-Dimethyl | 2-Amino-3,4-dimethyl-N—[4-(1H—imidazol-1-yl)butyl]benzamide | viscous oil |
| 6 | 3,5-Dichloro | 2-Amino-3,5-dichloro-N—[4-(1H—imidazol-1-yl)butyl]benzamide | viscous oil |
| 7 | 4-Chloro | 2-Amino-4-chloro-N—[4-(1H—imidazol-1-yl)butyl]benzamide hydrate | 103–105 |

EXAMPLE 8

2-Amino-N-[3-(1H-imidazol-1-yl)-2-methylpropyl]benzamide

A mixture of 8.15 g of isatoic anhydride, 6.7 ml of 3-(1H-imidazol-1-yl)-2-methylpropanamine and 40 ml of dimethyl sulfoxide was stirred for 20 hours at room temperature and then treated with 100 ml of water, 25 ml of 1N sodium hydroxide and 300 ml of methylene chloride. The layers were separated and the organic layer was washed with water, dried over magnesium sulfate and concentrated. The viscous residue was triturated with ether and the desired product precipitated, mp 116°–119° C.

Following the procedure of this example and using the appropriate isatoic anhydride, the products of Examples 9–12 were obtained as set forth in Table IV below.

TABLE IV

| Ex. | Isatoic Anhydride | Product | MP °C. |
| --- | --- | --- | --- |
| 9 | 5-Bromo | 2-Amino-5-bromo-N—[3-(1H—imidazol-1-yl)-2-methyl-propyl]benzamide | 166–164 |
| 10 | 5-Nitro | 2-Amino-N—[3-(1H—imidazol-1-yl)-2-methylpropyl]-5-nitro-benzamide | 157–159 |
| 11 | 5-Methyl | 2-Amino-N—[3-(1H—imidazol-1-yl)-2-methylpropyl]-5-methyl-benzamide, hemihydrate | 120–122 |
| 12 | 5-Chloro | 2-Amino-5-chloro-N—[3-(1H—imidazol-1-yl)-2-methyl-propyl]benzamide | 149–155 |

EXAMPLE 13

2-Amino-N-[3-(1H-imidazol-1-yl)propyl]benzamide

A mixture of 2.93 g of isatoic anhydride, 2.50 g of 1H-imidazol-1-propanamine and 30 ml of toluene was heated at 90° C. for 45 minutes and cooled. The toluene layer was decanted and the residue was dissolved in methylene chloride, washed with dilute sodium hydroxide solution, water and dried over magnesium sulfate. The organic layer was concentrated to obtain the desired product, mp 107°–110° C.

EXAMPLE 14

2-Amino-5-chloro-N-[3-(1H-imidazol-1-yl)propyl]benzamide

A mixture of 7.92 g of 5-chloroisatoic anhydride, 5.0 g of 1H-imidazole-1-propanamine and 75 ml of ethanol was stirred at room temperature for 20 hours and concentrated. The residue was washed onto a filter with ethanol, then washed with ether to give the desired product, mp 155°–157° C.

EXAMPLE 15

2-Amino-5-Chloro-N-[3-(1H-1,2,4-triazol-1-yl)-propyl]benzamide

When 5-chloroisatoic anhydride was reacted with 3-(1H-1,2,4-triazol-1-yl)propylamine by the procedure of Example 14, this compound, mp 116°–118° C., was obtained.

EXAMPLE 16

3-[4-(1H-Imidazol-1-yl)butyl]-1,2,3-benzotriazin-4(3H)-one

A solution of 2.58 g of 2-amino-N-[4-(1H-imidazol-1-yl)butyl]benzamide in 15 ml of water and 4.1 ml of concentrated hydrochloric acid was stirred in an ice bath. A solution of 0.72 g of sodium nitrite in 10 ml of water was added dropwise and the mixtue was stirred for 60 minutes and treated with 5 ml of 10N sodium hydroxide. After 60 minutes, acetic acid was added to a pH of 6–7. The desired product was filtered off and dried in vacuo, mp 96°–98° C.

Following the procedure of this example and using the appropriate benzamide derivative, the products of Examples 17–18 were obtained as set forth in Table V.

TABLE V

| Ex. | Benzamide | Product | MP °C. |
| --- | --- | --- | --- |
| 17 | Ex. 13 | 3-[3-(1H—Imidazol-1-yl)propyl]-1,2,3-benzotriazin-4(3H)—one | 85–87 |
| 18 | Ex. 14 | 6-Chloro-3-[3-(1H—imidazol-1-yl)-propyl]-1,2,3-benzotriazin-4(3H)—one | 65–70 |

EXAMPLE 19

6-Chloro-3-[3-(1H-imidazol-1-yl)-2-methylpropyl]-1,2,3-benzotriazin-4(3H)-one A solution of 5.86 g of 2-amino-5-chloro-N-[3-(1H-imidazol-1-yl)-2-methylpropyl]benzamide in 30 ml of water and 8.3 ml of concentrated hydrochloric acid was cooled in an ice bath and a solution of 1.42 g of sodium nitrite in 10 ml of water was added dropwise. The mixture was stirred, treated for 50 minutes with 10 ml of 10N sodium hydroxide, stirred for 50 minutes and acetic acid was added until a pH of 6–7 was reached. The product was extracted into methylene chloride and the organic layer was washed with water, dried over magnesium sulfate and concentrated. Treatment with ethyl ether resulted in crystals of the desired product, mp 100°-102° C. A sample was converted to the hydrochloride salt, mp 185°-188° C.

Following the procedure of this example and using the appropriate benzamide derivative, the products of Examples 20-30 were obtained as set forth in Table VI.

TABLE VI

| Ex. | Benzamide | Product | MP °C. |
|---|---|---|---|
| 20 | Ex. 8 | 3-[3-(1H—Imidazol-1-yl)-2-methylpropyl]-1,2,3-benzotriazin-4(3H)—one, monohydrochloride | 180-182 |
| 21 | Ex. 15 | 6-Chloro-3-[3-(1,2,4-triazin-1-yl)propyl]-1,2,3-benzotriazin-4(3H)—one | 110-112 |
| 22 | Ex. 7 | 7-Chloro-3-[4-(1H—imidazol-1-yl)butyl]-1,2,3-benzotriazin-4(3H)—one | 123-125 |
| 23 | Ex. 6 | 6,8-Dichloro-3-[4-(1H—imidazol-1-yl)butyl]-1,2,3-benzotriazin-4(3H)—one, monohydrochloride | 227-229 |
| 24 | Ex. 2 | 6-Bromo-3-[4-(1H—imidazol-1-yl)butyl]-1,2,3-benzotriazin-4(3H)—one, monohydrochloride | 203-205 |
| 25 | Ex. 9 | 6-Bromo-3-[3-(1H—imidazol-1-yl)-2-methylpropyl]-1,2,3-benzotriazin-4(3H)—one | 120-122 |
| 26 | Ex. 4 | 3-[4-(1H—Imidazol-1-yl)butyl]-6-methyl-1,2,3-benzotriazin-4(3H)—one | 86-90 |
| 27 | Ex. 11 | 3-[3-(1H—Imidazol-1-yl)-2-methylpropyl]-6-methyl-1,2,3-benzotriazin-4(3H)—one, monohydrochloride | 162-165 |
| 28 | Ex. 5 | 3-[4-(1H—Imidazol-1-yl)butyl]-7,8-dimethyl-1,2,3-benzotriazin-4(3H)—one, monohydrochloride | 181-183 |
| 29 | Ex. 10 | 3-[3-(1H—Imidazol-1-yl)-2-methylpropyl]-6-nitro-1,2,3-benzotriazin-4(3H)—one, hydrate | 90-110 |
| 30 | Ex. 3 | 6-Chloro-3-[4-(1H—imidazol-1-yl)butyl]-1,2,3-benzotriazin-4(3H)—one | 121-123 |

EXAMPLE 31

6-Chloro-3-[8-(1H-imidazol-1-yl)octyl]-1,2,3-benzotriazin-4(3H)-one

A mixture of 1.98 g of 5-chloroisatoic anhydride, 1.95 g imidazole-1-octanamine and 10 ml of dimethyl sulfoxide was stirred at room temperature for 20 hours. Water, methylene chloride and 5 ml of 1N sodium hydroxide were added and the layers were separated. The organic layer was washed with water, dried over magnesium sulfate and concentrated to an oily residue. This material was mixed with 15 ml of water and 4.2 ml of concentrated hydrochloric acid and cooled in an ice bath while a solution of 0.72 g of sodium nitrite in 10 ml of water was added dropwise. The mixture was stirred for one hour and 5 ml of 10N sodium hydroxide was added. After one hour, the pH of the reaction mixture was adjusted to 6-7 and the desired product was extracted into methylene chloride. This solution was washed with water, dried over magnesium sulfate and concentrated. Trituration with ether resulted in the desired product, mp 45° C. The hydrochloride salt was prepared by treatment with ethanolic hydrogen chloride and ether, mp 140°-142° C.

Following the procedure of this example and using the appropriate intermediate, the products of Examples 32-37 were obtained as set forth in Table VII.

TABLE VII

| Ex. | Isatoic Anhydride | Amine | Product | MP °C. |
|---|---|---|---|---|
| 32 | H | 4-(3-Pyridinyl)butanamine | 3-[4-(3-Pyridinyl)butyl]-1,2,3-benzotriazin-4(3H)—one | 74-75 |
| 33 | 5-Cl | Imidazole-1-decanamine | 6-Chloro-3-[10-(1H—imidazol-1-yl)decyl]-1,2,3-benzotriazin-4(3H)—one, fumarate | 150-153 |
| 34 | 5-Cl | 4-methyl-1H—imidazole-1-propanamine | 6-Chloro-3-[3-(4-methyl-1H—imidazol-1-yl)propyl]-1,2,3-benzotriazin-4(3H)—one | 119-138 |
| 35 | 5-Cl | 4-(3-Pyridinyl)butanamine | 6-Chloro-3-[4-(3-pyridinyl)butyl]-1,2,3-benzotriazin-4(3H)—one | 92-94 |
| 36 | 3-CF$_3$ | Imidazole-1-butanamine | 3-[4-(1H—Imidazol-1-yl)butyl]-8-trifluoromethyl-1,2,3-benzotriazin-4(3H)—one | 116-118 |
| 37 | 3-CF$_3$ | Imidazole-1-pentanamine | 3-[5-(1H—Imidazol-1-yl)pentyl]-8-trifluoromethyl-1,2,3-benzotriazin-4(3H)—one | 88-90 |

EXAMPLE 38

3-[3-(2-Phenyl-1H-imidazol-1-yl)propyl]-1,2,3-benzotriazin-4(3H)-one

The above compound is obtained when isatoic anhydride is reacted with 2-phenyl-1H-imidazole-1-propanamine by the procedure of Example 31.

EXAMPLE 39

6-Fluoro-3-[4-(1H-imidazol-1-yl)butyl]-1,2,3-benzotriazin-4(3H)-one

When 5-fluoroisatoic anhydride is reacted with imidazole-1-butanamine by the procedure of Example 31, this compound is obtained.

EXAMPLE 40

8-Chloro-3-[4-(1H-imidazol-1-yl)butyl]-1,2,3-benzotriazine-4(3H)-one

When 3-chloroisatoic anhydride is reacted with imidazole-1-butanamine by the procedure of Example 31, the above compound is obtained.

EXAMPLE 41

6-Chloro-3-[5-(1H-imidazol-1-yl)pentyl]-1,2,3-benzotriazin-4(3H)-one

A mixture of 1.98 g of 5-chloroisatoic anhydride, 25 ml of ethanol and 1.57 g of imidazole-1-pentanamine was stirred at room temperature for 18 hours, then concentrated. The residue was dissolved in 15 ml of water and 4.0 ml of concentrated hydrochloric acid, then cooled in an ice bath while a solution of 0.72 g of sodium nitrite in 10 ml of water was added. After one hour, 5 ml of 10N sodium hydroxide was added and the mixture was stirred for one hour. The pH was then adjusted with acetic acid to 6-7. The mixture was extracted with methylene chloride, washed with water and concentrated. The residual oil was purified by high pressure liquid chromatography and developed with ethyl acetate on a silica gel column. The desired product melted at 80°–82° C. The hydrochloride salt was prepared, mp 206°–210° C.

The procedure of this example was followed using the appropriate intermediate to prepare the products of Examples 42–44, as set forth in Table VIII.

TABLE VIII

| Ex. | Isatoic Anhydride | Amine | Product | MP °C. |
|---|---|---|---|---|
| 42 | 5-Cl | Imidazole-1-hexanamine | 6-Chloro-3-[6-(1H—imidazol-1-yl)hexyl]-1,2,3-benzotriazin-4(3H)—one | 99–101 |
| 43 | H | Imidazole-1-pentanamine | 3-[5-(1H—Imidazol-1-yl)pentyl]-1,2,3-benzotriazin-4(3H)—one, monohydrochloride | 188–190 |
| 44 | H | Imidazole-1-hexanamine | 3-[6-(1H—Imidazol-1-yl)hexyl]-1,2,3-benzotriazin-4(3H)—one, monohydrochloride | 155–156 |

EXAMPLE 45

3-[4-(1H-Imidazol-1-yl)butyl]-6-methoxy-1,2,3-benzotriazin-4(3H)-one

The above compound is obtained when 5-methoxyisatoic anhydride is reacted with imidazole-1-butanamine by the procedure of Example 41.

EXAMPLE 46

3-[3-(4-Ethyl-1H-imidazol-1-yl)propyl]-1,2,3-benzotriazin-4(3H)-one

When 4-ethyl-1H-imidazole-1-propanamine is reacted with isatoic anhydride by the procedure of Example 41, the above compound is obtained.

EXAMPLE 47

3-[4-(1H-Imidazol-1-yl)-2-butenyl]-1,2,3-benzotriazin-4(3H)-one

When isatoic anhydride is reacted with 4-(1H-imidazol-1-yl)-2-butenamine by the procedure of Example 41, the above compound is obtained.

EXAMPLE 48

3-[3-(1H-Imidazol-1-yl)-3-phenylpropyl]-1,2,3-benzotriazin-4(3H)-one

This compound is obtained when isatoic anhydride is reacted with 3-(1H-imidazol-1-yl)-3-phenylpropanamine by the procedure of Example 41.

EXAMPLE 49

6-Amino-3-[3-(1H-imidazol-1-yl)-2-methylpropyl]-1,2,3-benzotriazin-4(3H)-one

A mixture of 1.0 g of 3-[3-(1H-imidazol-1-yl)-2-methylpropyl]-6-nitro-1,2,3-benzotriazin-4(3H)-one, 2.0 g of 10% palladium on carbon catalyst and 200 ml of ethanol is shaken in a Parr hydrogenator under 45 pounds of hydrogen pressure until the theoretical amount of hydrogen is absorbed. The reaction mixture is heated to the boil and the catalyst is filtered off. The ethanolic solution is concentrated to a low volume and the desired product is recovered.

We claim:

1. A compound selected from the group consisting of those of the formula:

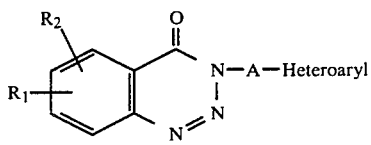

wherein A is a divalent moiety of the formula:

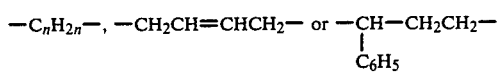

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

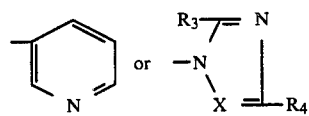

wherein $R_3$ and $R_4$ may be hydrogen, alkyl having from one to four carbon atoms or phenyl and X is CH or N; together with the pharmaceutically acceptable salts thereof.

2. The compound according to claim 1 which is 3-[3-(1H-imidazol-1-yl)propyl]-1,2,3-benzotriazin-4(3H)-one.

3. The compound according to claim 1 which is 3-[4-(1H-imidazol-1-yl)butyl]-1,2,3-benzotriazin-4(3H)-one.

4. The compound according to claim 1 which is 3-[5-(1H-imidazol-1-yl)pentyl]-1,2,3-benzotriazin-4(3H)-one, monohydrochloride.

5. The compound according to claim 1 which is 3-[6-(1H-imidazol-1-yl)hexyl]-1,2,3-benzotriazin-4(3H)-one, monohydrochloride.

6. The compound according to claim 1 which is 6-chloro-3-[4-(1H-imidazol-1-yl)butyl]-1,2,3-benzotriazin-4(3H)-one.

7. The compound according to claim 1 which is 6-bromo-3-[4-(1H-imidazol-1-yl)butyl]-1,2,3-benzotriazin-4(3H)-one, monohydrochloride.

8. The compound according to claim 1 which is 6-chloro-3-[6-(1H-imidazol-1-yl)hexyl]-1,2,3-benzotriazin-4(3H)-one.

9. The compound according to claim 1 which is 6-chloro-3-[8-(1H-imidazol-1-yl)octyl]-1,2,3-benzotriazin-4(3H)-one, monohydrochloride.

10. The compound according to claim 1 which is 6,8-dichloro-3-[4-(1H-imidazol-1-yl)butyl]-1,2,3-benzotriazin-4(3H)-one, monohydrochloride.

11. The compound according to claim 1 which is 3-[4-(1H-imidazol-1-yl)butyl]-6-methyl-1,2,3-benzotriazin-4(3H)-one.

12. The compound according to claim 1 which is 3-[3-(1H-imidazol-1-yl)-2-methylpropyl]-1,2,3-benzotriazin-4(3H)-one, monohydrochloride.

13. The compound according to claim 1 which is 6-chloro-3-[3-(1H-imidazol-1-yl)-2-methylpropyl]-1,2,3-benzotriazin-4(3H)-one.

14. A method of inhibiting thromboxane synthetase enzyme in a mammal which comprises administering internally to said mammal a thromboxane synthetase enzyme inhibiting amount of a compound selected from those of the formula:

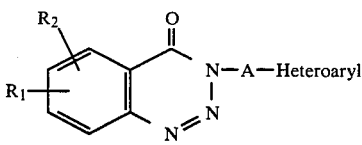

wherein A is a divalent moiety of the formula:

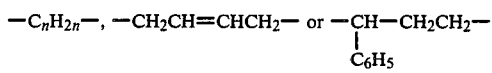

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

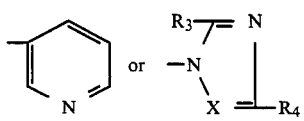

wherein $R_3$ and $R_4$ may be hydrogen, alkyl having from one to four carbon atoms or phenyl and X is CH or N; together with the pharmaceutically acceptable salts thereof.

15. A therapeutic composition of matter in dosage unit form comprising from about 10 mg to about 700 mg of a compound selected from those of the formula:

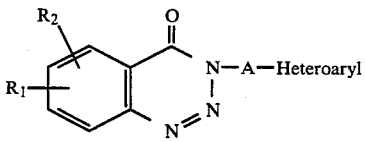

wherein A is a divalent moiety of the formula:

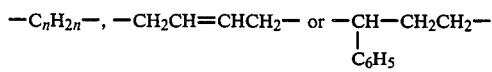

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

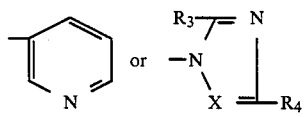

wherein $R_3$ and $R_4$ may be hydrogen, alkyl having from one to four carbon atoms or phenyl and X is CH or N; together with the pharmaceutically acceptable salts thereof in association with a pharmaceutically acceptable carrier.

16. A method of lowering elevated blood pressure in a mammal which comprises administering internally to said mammal an antihypertensive amount of a compound selected from the group consisting of those of the formula:

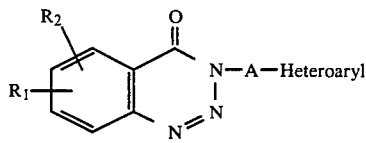

wherein A is a divalent moiety of the formula:

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

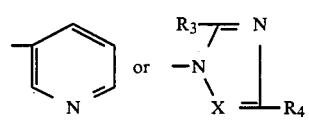

wherein $R_3$ and $R_4$ may be hydrogen, alkyl having from one to four carbon atoms or phenyl and X is CH or N; together with the pharmaceutically acceptable salts thereof.

17. A method of treating thrombotic diseases in a mammal which comprises administering internally to said mammal an antithrombotic amount of a compound selected from those of the formula:

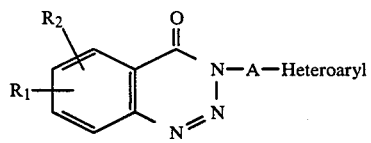

wherein A is a divalent moiety of the formula:

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

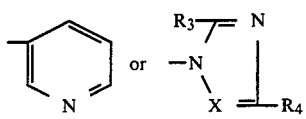

wherein $R_3$ and $R_4$ may be hydrogen, alkyl having from one to four carbon atoms or phenyl and X is CH or N; together with the pharmaceutically acceptable salts thereof.

18. A method of treating ischemic vascular disease in mammals which comprises administering internally to said mammals an anti-ischemic amount of a compound selected from those of the formula:

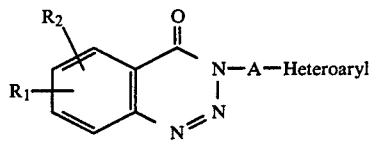

wherein A is a divalent moiety of the formula:

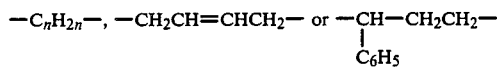

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

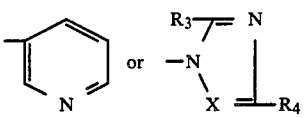

wherein $R_3$ and $R_4$ may be hydrogen, alkyl having from one to four carbon atoms or phenyl and X is CH or N; together with the pharmaceutically acceptable salts thereof.

19. A process for producing a compound of the formula:

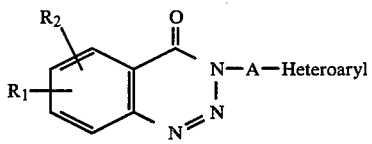

wherein A is a divalent moiety of the formula:

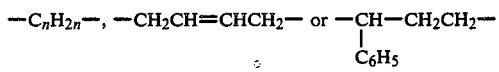

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

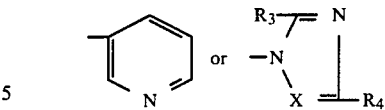

wherein $R_3$ and $R_4$ may be hydrogen, alkyl having from one to four carbon atoms or phenyl and X is CH or N; together with the pharmaceutically acceptable salts thereof; which comprises reacting a substituted isatoic anhydride of the formula:

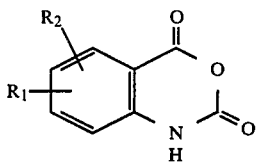

where $R_1$ and $R_2$ are as described above with a heterocyclic alkanamine of the formula:

$H_2N-A-$Heteroaryl where A and Heteroaryl are as described hereinabove, in an inert solvent to provide an intermediate of the formula:

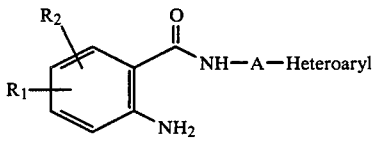

and treating said intermediate amide with sodium nitrite in dilute hydrochloric acid, then neutralizing the mixture with dilute sodium hydroxide and recovering the compound initially defined herein.

20. A method of treating migraine headaches in a mammal which comprises administering internally to said mammal a migraine-ameliorating amount of a compound selected from those of the formula:

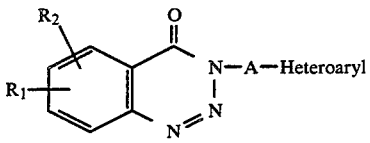

wherein A is a divalent moiety of the formula:

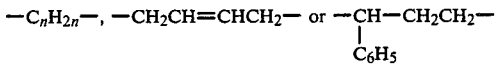

wherein n is an integer from 3 to 10, inclusive; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

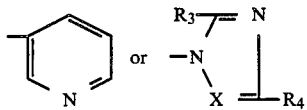

wherein $R_3$ and $R_4$ may be hydrogen, alkyl having from one to four carbon atoms or phenyl and X is CH or N; together with the pharmaceutically acceptable salts thereof.

* * * * *